United States Patent
Jung et al.

(10) Patent No.: US 8,872,140 B2
(45) Date of Patent: Oct. 28, 2014

(54) TARGET FOR GENERATING CARBON IONS AND TREATMENT APPARATUS USING THE SAME

(75) Inventors: Moon Youn Jung, Daejeon (KR); Nam Soo Myung, Seongnam (KR); Hyung Ju Park, Suwon (KR); Seunghwan Kim, Daejeon (KR)

(73) Assignee: Electronics and Telecommunications Research Institute, Daejeon (KR)

( * ) Notice: Subject to any disclaimer, the term of this patent is extended or adjusted under 35 U.S.C. 154(b) by 198 days.

(21) Appl. No.: 13/593,353

(22) Filed: Aug. 23, 2012

(65) Prior Publication Data
US 2013/0138184 A1 May 30, 2013

(30) Foreign Application Priority Data
Nov. 30, 2011 (KR) .................. 10-2011-0126763

(51) Int. Cl.
| | | |
|---|---|---|
| *A61N 5/10* | (2006.01) | |
| *H01J 37/08* | (2006.01) | |
| *H01J 27/02* | (2006.01) | |
| *H01J 27/24* | (2006.01) | |

(52) U.S. Cl.
CPC . *A61N 5/10* (2013.01); *H01J 37/08* (2013.01); *H01J 2237/08* (2013.01); *H01J 27/24* (2013.01); *H01J 27/02* (2013.01)
USPC .................... 250/492.3; 250/423 P

(58) Field of Classification Search
CPC ....... H01J 37/08; H01J 2237/08; H01J 27/02; H01J 27/24; A61N 5/10
USPC ..................................... 250/492.3
See application file for complete search history.

(56) References Cited

U.S. PATENT DOCUMENTS

| | | | | |
|---|---|---|---|---|
| 5,406,906 | A * | 4/1995 | Rimai et al. .............. | 117/92 |
| 7,906,769 | B2 * | 3/2011 | Blasche et al. ........... | 250/492.3 |
| 8,315,039 | B2 * | 11/2012 | Zhamu et al. ............ | 361/502 |
| 8,409,450 | B2 * | 4/2013 | Zettl et al. ................ | 216/7 |
| 2010/0126660 | A1 * | 5/2010 | O'Hara ..................... | 156/249 |
| 2011/0189406 | A1 * | 8/2011 | Cho et al. ................. | 427/523 |
| 2013/0178689 | A1 * | 7/2013 | Jung et al. ................ | 600/1 |

FOREIGN PATENT DOCUMENTS

KR         101176544 B1 *  8/2012

OTHER PUBLICATIONS

A. A. Gonoskov et al., "Multicascade Proton Acceleration by a Superintense Laser Pulse in the Regime of Relativistically Induced Slab Transparency", PRL 102, May 8, 2009, pp. 184801-1~184801-4, The American Physical Society.

* cited by examiner

*Primary Examiner* — Jack Berman

(57) ABSTRACT

Provided are a carbon ion generation target and a treatment apparatus including the same. The treatment apparatus includes a support member, a carbon ion generation target fixed to the support member, and a laser for irradiating laser beam into the carbon ion generation target to generate carbon ions from the carbon ion generation target, thereby projecting the carbon ions onto a tumor portion of a patient. Here, the carbon ion generation target includes a substrate and carbon thin films disposed on the substrate.

15 Claims, 4 Drawing Sheets

TARGET FOR GENERATING CARBON IONS AND TREATMENT APPARATUS USING THE SAME

CROSS-REFERENCE TO RELATED APPLICATIONS

This U.S. non-provisional patent application claims priority under 35 U.S.C. §119 of Korean Patent Application No. 10-2011-0126763, filed on Nov. 30, 2011, the entire contents of which are hereby incorporated by reference.

BACKGROUND OF THE INVENTION

The present invention relates to a treatment apparatus, and more particularly, to a target for generating carbon ions and a tumor treatment apparatus using the same.

Methods for radiotherapy may include X-ray treatments, electron beam treatments, and ion beam treatments. Among these, since the X-ray treatments are the cheapest treatment methods which can be realized using the simplest device, the X-ray treatments are being most commonly used at the present day. Although it has been proven in 1950's that tumors can be treated by accelerating electrons using an accelerator to inject the electrons into the tumors, with the miniaturization of an electron accelerator in 1980's, the electron beam treatments have been taken over as one method for radiotherapy. In the X-ray treatments or the electron beam treatments, hydrogen bonds within cancer cells can be cut to destroy DNAs of the cancel cells. However, side effects in which healthy cells existing within the traveling path of X-rays or electron beams are seriously damaged may occur. Technologies such as intensity-modulated radiation therapy (IMRT), tomo therapy, and cyber knife have been developed as methods for reducing the radiation exposure of normal cells. However, the technologies can not completely solve the above-described side effects.

The ion beam treatments are in the spotlight as treatment methods which can mitigate the side effects due to the X-ray treatments or the electron beam treatments. To allow the ion beam to penetrate a material, the ion beam should be accelerated to have high velocity, like the electrons. Even though the ion beam is gradually decreased in velocity when the ion beam penetrates a certain material, the ion beam is subject to the most energy loss of ionizing radiation just before the ion beam is stopped. This phenomenon is called a Bragg peak after William Henry Bragg, which discovered the phenomenon in 1903. Thus, in a case of such an ion beam treatment, malignant tumors may be selectively and locally treated when the ions are precisely controlled in velocity.

In aspect of acceleration energy, the lightest hydrogen ions (i.e., protons) of ions have been considered as a material for ion beam treatments. However, carbon ion treatments are in the spotlight as tumor treatment methods in recent years after it is known that carbons have superior biological effects than protons. For example, according to researches, carbon has a cancer cell destruction rate greater by about 2.8 times than that of protons and results in a cancer recurrence rate less by about 2.5 times than that resulted from X-rays or protons. In general, carbon ions may be accelerated by a synchrotron or cyclotron device. However, since the synchrotron or cyclotron device is large and expensive, commercial applicability thereof is low.

SUMMARY OF THE INVENTION

The present invention provides a carbon ion generation target which can generate highly pure carbon ions and a tumor treatment apparatus using the same.

The present invention also provides a carbon ion generation target having high commercial applicability and a tumor treatment apparatus using the same.

Embodiments of the present invention provide treatment apparatuses including: a support member; a carbon ion generation target fixed to the support member; and a laser for providing a laser beam to the carbon ion generation target to generate carbon ions from the carbon ion generation target and project the carbon ions onto a tumor portion of a patient, wherein the carbon ion generation target includes a substrate and carbon thin films provided on the substrate.

In some embodiments, the carbon thin films may include graphene layers.

In other embodiments, treatment apparatuses may further include spacers in the grapheme layers, the spacers separating the graphene layers apart from each other by a predetermined distance.

In still other embodiments, the laser may include a high-output ultrapulse laser.

In other embodiments of the present invention, carbon ion generation targets include: a substrate; and carbon thin films provided on the substrate.

In some embodiments, the carbon thin films may include graphene layers.

In other embodiments, carbon ion generation targets may further include spacers in the grapheme layers, the spacers separating the graphene layers apart from each other by a predetermined distance.

In still other embodiments, the spacers may be ball type spacers.

In even other embodiments, the spacers may have diameters of about 1 micrometer to about 20 micrometers.

In yet other embodiments, the spacers may include at least one of silicon oxides, metals, and polymers.

In further embodiments, the carbon thin films may further include at least one of a fullerene layer and carbon nanotubes in which carbon atoms of the graphene layers are connected in a globular shape or pillar shape.

In still further embodiments, the substrate may include a grid for supporting the carbon thin films.

In even further embodiments, the substrate may further include a window through which the carbon thin films supported by the grids are exposed downward.

In yet further embodiments, the grid may include a metal or silicon material.

In much further embodiments, the substrate may include a silicon wafer or a silicon bar.

In still other embodiments of the present invention, methods for manufacturing a carbon ion generation target include: providing a substrate; and forming carbon thin films on the substrate.

In some embodiments, the carbon thin films may include graphene layers formed by at least one of a transferring method, a chemical vapor deposition method, and a liquid deposition method.

In other embodiments, methods may further include scattering spacers between the graphene layers.

In still other embodiments, the spacers may be scattered between the graphene layers in a spray manner.

In even other embodiments, the spacers may be scattered between the graphene layers by a volatile solvent.

BRIEF DESCRIPTION OF THE DRAWINGS

The accompanying drawings are included to provide a further understanding of the present invention, and are incorporated in and constitute a part of this specification. The drawings illustrate exemplary embodiments of the present invention and, together with the description, serve to explain principles of the present invention. In the drawings.

DETAILED DESCRIPTION OF PREFERRED EMBODIMENTS

Figure 1:
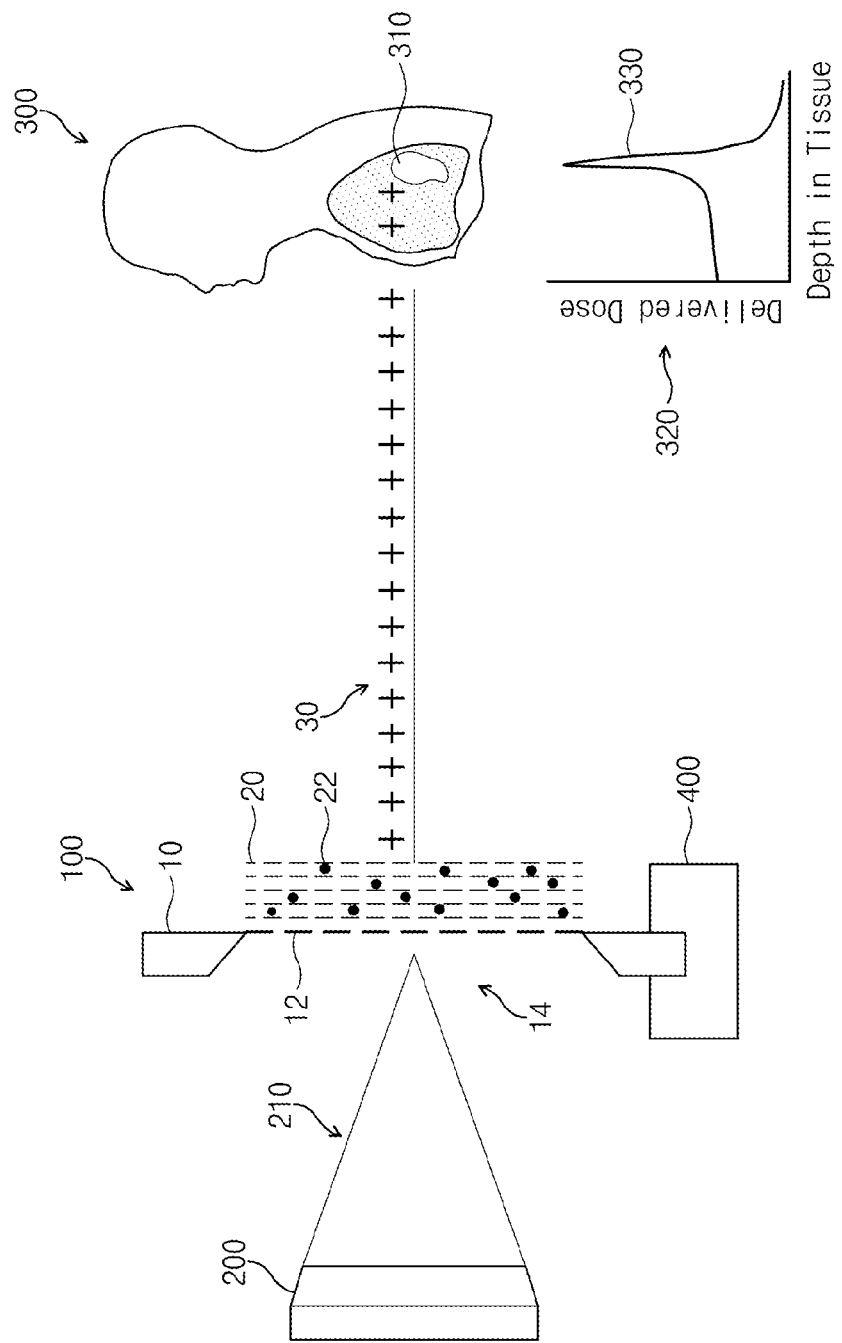
FIG. 1 is a schematic view of a tumor treatment apparatus using a carbon ion generation target according to an embodiment of the inventive concept.

Preferred embodiments of the present invention will be described below in more detail with reference to the accompanying drawings. Advantages and features of the present invention, and implementation methods thereof will be clarified through following embodiments described with reference to the accompanying drawings. The present invention may, however, be embodied in different forms and should not be construed as limited to the embodiments set forth herein. Rather, these embodiments are provided so that this disclosure will be thorough and complete, and will fully convey the scope of the present invention to those skilled in the art. In the drawings, the dimensions of layers and regions are exaggerated for clarity of illustration.

In the following description, the technical terms are used only for explain a specific exemplary embodiment while not limiting the present invention. The terms of a singular form may include plural forms unless referred to the contrary. The meaning of "include," "comprise," "including," or "comprising," specifies a property, a region, a fixed number, a step, a process, an element and/or a component but does not exclude other properties, regions, fixed numbers, steps, processes, elements and/or components. Since preferred embodiments are provided below, the order of the reference numerals given in the description is not limited thereto. It will be understood that when an element such as a layer, film, region, or substrate is referred to as being "on" another element, it can be directly on the other element or intervening elements may also be present.

Additionally, the embodiment in the detailed description will be described with sectional views as ideal exemplary views of the present invention. In the figures, the dimensions of layers and regions are exaggerated for clarity of illustration. Accordingly, shapes of the exemplary views may be modified according to manufacturing techniques and/or allowable errors. Therefore, the embodiments of the present invention are not limited to the specific shape illustrated in the exemplary views, but may include other shapes that may be created according to manufacturing processes. For example, an etched region illustrated or described as a rectangle will, typically, have rounded or curved features. Thus, the regions illustrated in the figures are schematic in nature and their shapes are not intended to illustrate the precise shape of a region of a device and are not intended to limit the scope of the present invention.

FIG. 1 is a schematic view of a tumor treatment apparatus using a carbon ion generation target according to an embodiment of the inventive concept.

Referring to FIG. 1, a tumor treatment apparatus according to the present invention may include a target 100 for generating carbon ions 30 (hereinafter, referred to as a carbon ion generation target 100) by a laser beam 210. The carbon ion generation target 100 may include graphene layers 20, which are sources of carbon ions 30. Carbon ions 30 may be discharged from the carbon ion generation target 100 in proportion to the intensity of a laser beam 210. A laser 200 may include a high-output ultrapulse laser capable of generating a femtosecond ($10^{-15}$) pulse laser beam 210. The laser 200 may be much smaller and less expensive than a general synchrotron or cyclotron device.

Thus, the tumor treatment apparatus according to the current embodiment of the inventive concept may be increased or maximized in commercial applicability.

Figure 2:
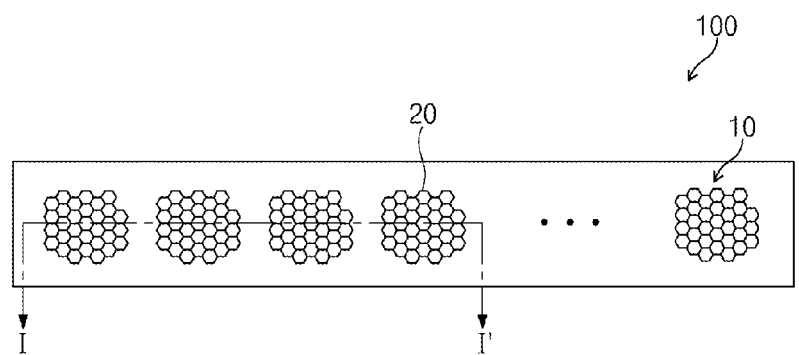
FIGS. 2 and 3 are plan views illustrating the carbon ion generation target of FIG. 1.
Figure 3:
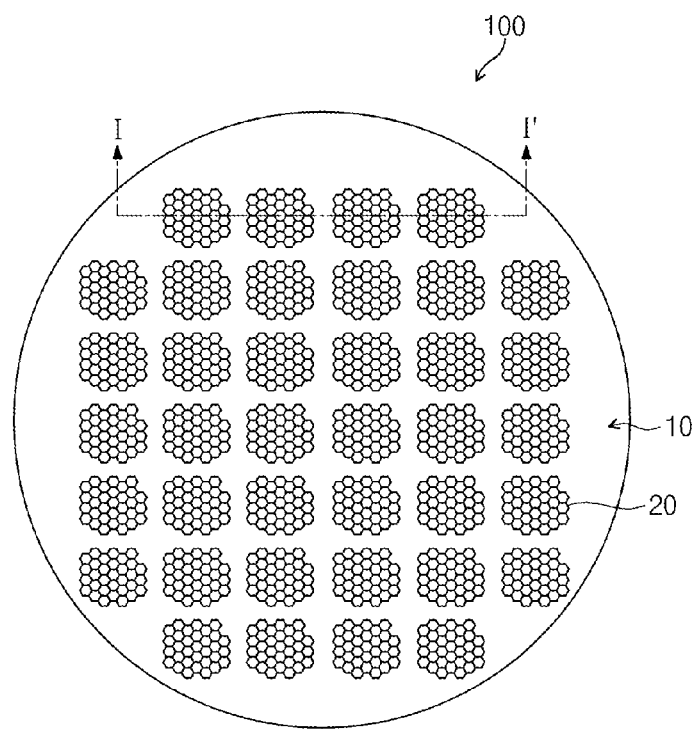
Figure 4:
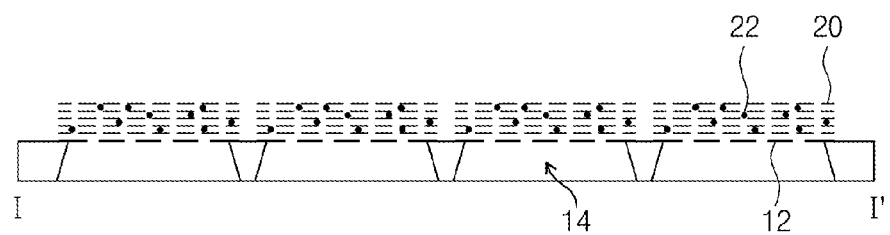
FIG. 4 is a sectional view taken along line I-I' of FIGS. 2 and 3.

FIGS. 2 and 3 are plan views illustrating the carbon ion generation target of FIG. 1. FIG. 4 is a sectional view taken along line I-I' of FIGS. 2 and 3.

Referring to FIGS. 1 to 4, the graphene layers 20 may be disposed on windows 14 of a substrate 10. The graphene layers 20 may be exposed downward from the substrate 10 through the windows 14. The graphene layers 20 may be carbon thin films in which carbon atoms arranged in a hexagonal alveolate shape are accumulated on top of another. The carbon thin films may further include carbon nanotubes or fullerenes. The graphene layers 20 may be two to fifty in number and may be stacked on each other. The graphene layers 20 may be spaced apart from each other at regular intervals by spacers 22. The spacers 22 may be ball type spacers having a thickness of about 1 μm to about 20 μm. The spacers 22 may include at least one material of silicon oxide ($SiO_2$), metal, and polymer.

The substrate 10 may be fixed by a support member 400. The support member 400 may include a holder for fixing the substrate 10. As described above, the substrate 10 may include the windows 14 for exposing the graphene layers 20. Grids 12 having a grating shape may be disposed within the windows 14. The grids 12 may support the graphene layers 20. The grids 12 may be include a metal or silicon material. The substrate 10 may include a silicon wafer or silicon bar which has a plurality of grids 12. The plurality of grids 12 in the silicon bar may be arranged in a line. Also, the silicon wafer may be a circular plate having a plurality of grids 12 arranged in a matrix or concentric shape. The grids 12 may include a mesh having a plurality of holes for exposing the graphene layers 20 downward. The grids 12 may be transmission electron microscopy (TEM) grids having a diameter of about 2 mm to about 4 mm.

If the graphene layers 20 are exposed to a laser beam 210, the graphene layers 20 may generate carbon ions 30. Here, the carbon ions 30 may have positive electrical properties because carbon atoms lose electrons. The carbon ions 30 may have energy in proportion to an output power of the laser beam 210. Thus, the carbon ion generation target 100 of the present invention can generate highly pure carbon ions using a laser beam 210.

The carbon ions 30 may penetrate organs or tissue of a human body 300 to reach a tumor portion 310. The penetration distance of each of the carbon ions 30 may be adjusted in proportion to the energy of the laser beam 210. The carbon ions 30 may be concentrated at a high concentration onto the tumor portion 310. For example, the carbon ions 30 may be concentrated at a delivered dose corresponding to a Bragg peak value 330 shown in a graph 320 of FIG. 1. Here, a horizontal axis of the graph 320 represents a depth in tissue of the human body 300, and a vertical axis represents delivered doses of the carbon ions 30. The Bragg peak value 330 may have a depth corresponding to a point at which each of particles such as the carbon ions 30 has a velocity of about zero because the particle with an electric charge having a high-energy state loses energy thereof by an opposite electric charge within a material to be penetrated when the particles penetrate the material.

Although not shown, the tumor portion 310 of the human body 300 may be detected by a detection device such as an X-ray image device, a magnetic resonance imaging (MRI) device, a computer tomography (CT) device, a positron emission tomography (PET) device, an ultrasonics wave device, or the like. The carbon ions 30 may have energy adjusted according to the output power of the laser beam 210 and may be concentrated onto the tumor portion 310 after penetrating the tissues of the human body 300. The carbon ions 30 may disturb tumor cells of the tumor portion 310 within the body of a patient. Particularly, the carbon ions 30 may disturb DNA double helices of the tumor cells or a metabolic process within nuclei of the tumor cells. Thus, the tumor cells may be thwarted in growth or necrotized by the carbon ions 30. As described above, the laser 200 may include the high-output ultrapulse laser.

Thus, the tumor treatment apparatus of the current embodiment of the inventive concept may be increased or maximized in commercial applicability.

A method for manufacturing a carbon ion generation target 100 according to an embodiment of the inventive concept will be described below.

FIGS. 5 to 9 are sectional views illustrating a process for manufacturing a carbon ion generation target according to an embodiment of the inventive concept.

Figure 5:
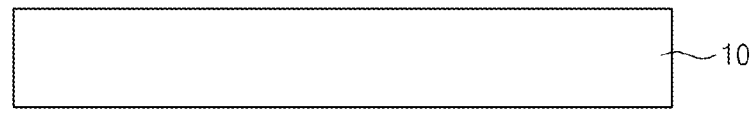
FIGS. 5 to 9 are sectional views illustrating a process for manufacturing a carbon ion generation target according to an embodiment of the inventive concept.

Referring to FIG. 5, a substrate 10 is provided. The substrate 10 may include a bulk type silicon wafer or silicon bar. Also, the substrate 10 may be a silicon-on-insulator (SOI) substrate. Although not shown, the SOI substrate may include a silicon substrate, an insulation layer formed on the silicon substrate, and a silicon bulk layer formed on the insulation layer.

Figure 6:
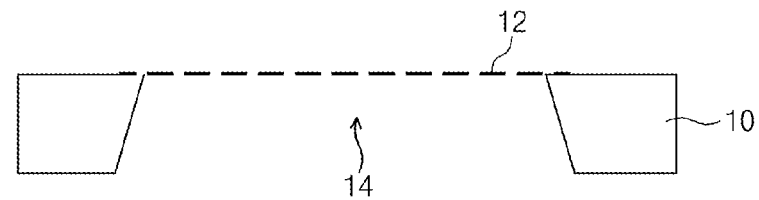

Referring to FIG. 6, a plurality of windows 14 and grids 12 are formed on the substrate 10. The windows 14 and the grids 12 may be formed using a general photolithograph process, an etch process, or an electron beam lithograph process. The photolithograph process may be a process for forming photoresist patterns (not shown) selectively exposing portions of the substrate 10 corresponding to the windows 14. Also, the etching process may be a process for selectively removing the portions of the substrate exposed by the photoresist patterns. The grids 12 may be formed by the electron beam lithograph process. The electron beam lithograph process may be a process for selectively removing the substrate 10 remaining on a bottom surface during the formation of the windows 14. Alternatively, the grids 12 may be separately mounted on the windows 14 of the substrate.

Figure 7:
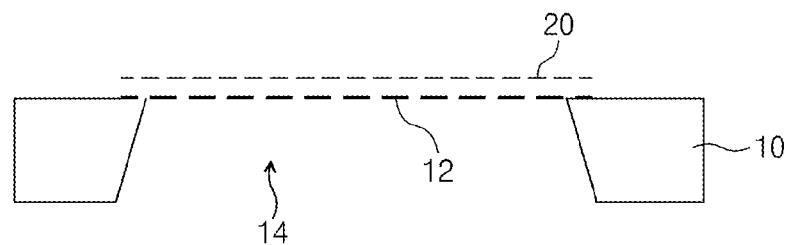

Referring to FIG. 7, a graphene layer 20 is formed on the grids 12. The graphene layer 20 may be formed through at least one of a transferring method, a chemical vapor deposition method, and a liquid deposition method. Here, the transferring method may be a method for forming the graphene layer 20 using a film on which an adhesive such as an adhesion tape is applied. Also, the graphene layer 20 may be formed by a chemical vapor deposition method and a liquid deposition method. First, graphene may be formed on a dummy substrate (not shown) using the chemical vapor deposition method. Then, the graphene may be floated by an etching solution for selectively removing the dummy substrate. Finally, the graphene layer 20 may be deposited on the substrate 10.

Figure 8:
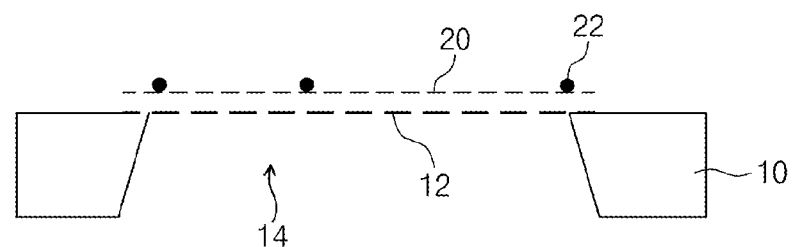

Referring to FIG. 8, spacers 22 are applied to a top surface of the graphene layer 20. The spacers may include at least one of silicon oxide particles, metal particles, and polymer particles. The spacers 22 may be applied to the top surface of the graphene layer 20 in a spray manner or blowing manner. Also, the spacers 22 may be scattered by a volatile solvent.

Figure 9:
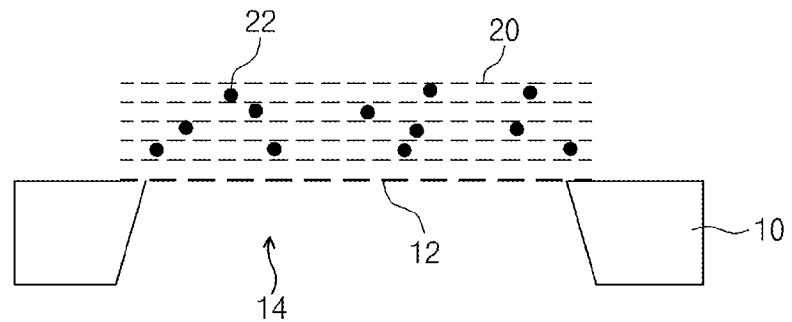

Referring to FIG. 9, the graphene layer 20 is formed again on the spacers 20. The graphene layer 20 may be formed through at least one of the transferring method, the chemical vapor deposition method, and the liquid deposition method. Thus, the spacers 22 and the graphene layers 20 may be formed alternately. For example, two to fifty graphene layers 20 may be formed.

Thus, in the method for manufacturing the carbon ion generation target 100 according to the present invention, since the graphene layers 20 are easily formed on the grids 12 of the substrate, the commercial applicability may be increased or maximized.

As described above, the plurality of graphene layers may be disposed on the grids of the substrate. The graphene layers may discharge the highly pure carbon ions by the laser beam. Also, the laser beam may be generated from the high-output ultrapulse laser which is much smaller and less expensive than the synchrotron or cyclotron device.

Thus, the carbon ion generation target and the treatment apparatus including the same according to the embodiment of the inventive concept may be increased or maximized in commercial applicability.

The above-disclosed subject matter is to be considered illustrative, and not restrictive, and the appended claims are intended to cover all such modifications, enhancements, and other embodiments, which fall within the true spirit and scope of the present invention. Thus, to the maximum extent allowed by law, the scope of the present invention is to be determined by the broadest permissible interpretation of the following claims and their equivalents, and shall not be restricted or limited by the foregoing detailed description.

What is claimed is:

1. A treatment apparatus comprising:
a support member;
a carbon ion generation target fixed to the support member; and
a laser for providing a laser beam to the carbon ion generation target to generate carbon ions from the carbon ion generation target and project the carbon ions onto a tumor portion of a patient,
wherein the carbon ion generation target comprises a substrate and carbon thin films provided on the substrate.

2. The treatment apparatus of claim 1, wherein the carbon thin films comprise graphene layers.

3. The treatment apparatus of claim 2, further comprising spacers in the graphene layers, the spacers separating the graphene layers apart from each other by a predetermined distance.

4. The treatment apparatus of claim 1, wherein the laser comprises a high-output ultrapulse laser.

5. The treatment apparatus of claim 3, wherein the spacers are ball type spacers.

6. The treatment apparatus of claim 5, wherein the spacers have diameters of about 1 micrometer to about 20 micrometers.

7. The treatment apparatus of claim 3, wherein the spacers comprise at least one of silicon oxides, metals, and polymers.

8. The treatment apparatus of claim 2, wherein the carbon thin films further comprise at least one of a fullerene layer and carbon nanotubes in which carbon atoms of the graphene layers are connected in a globular shape or pillar shape.

9. The treatment apparatus of claim 1, wherein the substrate comprises a grid for supporting the carbon thin films.

10. The treatment apparatus of claim 9, wherein the substrate further comprises a window through which the carbon thin films supported by the grid are exposed downward.

11. The treatment apparatus of claim 9, wherein the grid comprises a metal or silicon material.

12. The treatment apparatus of claim 9, wherein the substrate comprises a silicon wafer or a silicon bar.

13. A method for treating a patient, the method comprising:
generating carbon ions from a carbon ion generation target by exposing the carbon ion generation target to a laser beam, the carbon ion generation target including a substrate and carbon thin films provided on the substrate; and projecting the generated carbon ions onto a tumor portion of a patient.

14. The method of claim 13, wherein the carbon thin films include graphene layers that are a source of the carbon ions.

15. The method of claim 13, wherein generating carbon ions from the carbon ion generation target includes exposing the carbon ion generation target to a high-output ultrapulse laser beam.

* * * * *